(12) United States Patent
Jin et al.

(10) Patent No.: US 9,138,174 B2
(45) Date of Patent: Sep. 22, 2015

(54) DISPLACEMENT MEASUREMENT IN A FALL DETECTION SYSTEM

(75) Inventors: Sheng Jin, Shanghai (CN); Ningjiang Chen, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 739 days.

(21) Appl. No.: 12/991,713

(22) PCT Filed: May 5, 2009

(86) PCT No.: PCT/IB2009/051836
§ 371 (c)(1),
(2), (4) Date: Feb. 14, 2011

(87) PCT Pub. No.: WO2009/138900
PCT Pub. Date: Nov. 19, 2009

(65) Prior Publication Data
US 2011/0144542 A1  Jun. 16, 2011

(30) Foreign Application Priority Data
May 12, 2008  (CN) .......................... 2008 1 0097078

(51) Int. Cl.
*G08B 23/00* (2006.01)
*A61B 5/117* (2006.01)
*A61B 5/103* (2006.01)
*A61B 5/11* (2006.01)
*A61B 5/00* (2006.01)
*G08B 21/04* (2006.01)

(52) U.S. Cl.
CPC ............. *A61B 5/1117* (2013.01); *A61B 5/0002* (2013.01); *G08B 21/0446* (2013.01); *A61B 2562/0219* (2013.01)

(58) Field of Classification Search
CPC ...................................................... A61B 5/1117
USPC ................. 600/587, 595; 709/224; 340/573.7
See application file for complete search history.

(56) References Cited

U.S. PATENT DOCUMENTS 6,167,356 A   12/2000  Squadron et al.
6,201,476 B1   3/2001  Depeursinge et al.
(Continued)

FOREIGN PATENT DOCUMENTS

DE   4222373 A1   1/1994
EP   1195139 A1   4/2002
(Continued)

OTHER PUBLICATIONS

Kangas et al, Comparison of low-complexity fall detection algorithms for body attached accelerometers, 2008, Gait&Posture 28:285-291.*

(Continued)

*Primary Examiner* — Brian Szmal (57) ABSTRACT

There is provided a personal fall detection system comprising a sensor module that is suitable for attachment to a user, the sensor module comprising an accelerometer for measuring accelerations acting on the sensor module; and a processor for analyzing the measured accelerations to determine if the sensor module has suffered an impact, and for estimating a vertical displacement of the sensor module during a time period immediately before the impact; wherein the processor estimates the vertical displacement of the sensor module by twice integrating the measurements from the accelerometer.

21 Claims, 4 Drawing Sheets

(56) References Cited

U.S. PATENT DOCUMENTS

| | | |
|---|---|---|
| 2002/0103610 A1 | 8/2002 | Bachmann et al. |
| 2006/0020177 A1 | 1/2006 | Seo et al. |
| 2012/0059927 A1* | 3/2012 | Schieffelin et al. ........... 709/224 |

FOREIGN PATENT DOCUMENTS

| | | |
|---|---|---|
| EP | 1688746 A2 | 8/2006 |
| FR | 2829862 A1 | 3/2003 |
| GB | 2422790 A | 8/2006 |
| JP | 2005237576 A | 9/2005 |
| JP | 2005286809 A | 10/2005 |
| JP | 2006177749 A | 7/2006 |
| JP | 2007151948 A | 6/2007 |

OTHER PUBLICATIONS

Rodgers et al, Glossary of Biomechanical Terms, Concepts, and Units, 1984, Phys Ther. 64:1886-1902.*

Bourke et al: "The Identification of Vertical Velocity Profiles Using an Inertial Sensor to Investigate Pre-Impact Detection of Falls"; Medical Engineering & Physics, 2008, vol. 30, No. 7 pp. 937-946.

Kangas et al: "Determination of Simple Thresholds for Accelerometry-Based Parameters for Fall Detection"; Proceedings of the 29th Annual International Conference of the IEEE Engineering in Medicine and Biology Society (EMBS), 2007, pp. 1367-1370.

Noury et al: "Fall Detection-Principles and Methods"; Proceedings of the 29th Annual International Conference of the Engineering in Medicine and Biology Society (EMBS), 2007, pp. 1663-.

Bourke et al: "Evaluation of a Threshold-Based Tri-Axial Accelerometer Fall Detection Algorithm"; Gait & Posture, Jun. 2007, vol. 26, No. 2, pp. 194-199.

Nyan et al: "Distinguishing Fall Activities From Normal Activities by Angular Rate Characteristics and High-Speed Camera Characterization"; Medical Engineering & Physics, 2006, vol. 28, No. 8, pp. 842-849.

Lindemann et al: "Evaluation of a Fall Detector Based on Accelerometers: A Pilot Study"; Medical and Biological Engineering, 2005, vol. 43, No. 5, pp. 548-551.

* cited by examiner

DISPLACEMENT MEASUREMENT IN A FALL DETECTION SYSTEM

TECHNICAL FIELD OF THE INVENTION

The invention relates to the measurement of the displacement of an object, and in particular to a method and system for the measurement of the displacement of an object during a fall using an accelerometer.

BACKGROUND TO THE INVENTION

Three-dimensional accelerometers can be attached to objects, and can measure the acceleration of the object in three dimensions. As part of these measurements, the accelerometer measures accelerations on the object caused by gravity.

Generally, a personal fall detection system comprises a user worn sensor module that is arranged to wirelessly send out an alarm signal to the remaining part of the system in the event that an emergency situation is detected. Such a sensor module may comprise an alarm button that the user can press to have the module send out the alarm signal or a detector that detects if a user has fallen, whereby the sensor module automatically sends out an alarm signal.

Many existing automatic fall detection solutions are based on measuring acceleration of the daily activities and falls of the user with a fall detector attached to the body, usually at the waist. The basic principle of these fall detection solutions is to detect the large or significant impact caused by the body hitting the ground during a fall. Some solutions can also detect the change in orientation of the body caused by a fall, which improves the success rate in detecting falls.

However, the existing solutions still have an unacceptably high false alarm rate. This is because measuring the change in body orientation in conjunction with detecting the occurrence of a large impact is often not sufficient to distinguish all daily activities of a user from a fall.

The fall detection system can be provided with additional functionality to generate more information about the activities of the user, which can improve the performance. In particular, adding a displacement measurement sensor to the sensor module can improve the performance. This is because going from a standing position to falling onto the ground results in the height of the sensor module decreasing by about the height from the waist to the ground, if the sensor module is attached to the waist. This displacement information is useful for distinguishing some daily activities from falls and improves the fall detection performance.

Integrating a barometer into an accelerometer-based fall detection system that allows absolute height to be measured from air pressure, fulfills the above requirement. However, including this type of additional component in the sensor module leads to increased energy consumption and size for the system. In addition, measurements by barometers can be adversely affected by changes in the environment, such as a change in the ambient pressure or temperature.

Therefore, there is a need for an alternative methodology for measuring the displacement of a sensor module that includes an accelerometer.

SUMMARY OF THE INVENTION

According to a first aspect of the invention, there is provided a personal fall detection system comprising a sensor module that is suitable for attachment to a user, the sensor module comprising an accelerometer for measuring accelerations acting on the sensor module; and a processor for analyzing the measured accelerations to determine if the sensor module has suffered an impact, and for estimating a vertical displacement of the sensor module during a time period immediately before the impact; wherein the processor estimates the vertical displacement of the sensor module by twice integrating the measurements from the accelerometer.

Preferably, the processor is adapted to determine that the sensor module has suffered an impact if the measured accelerations are characteristic of a collision with a solid object.

Preferably, the processor is adapted to determine that the sensor module has suffered an impact if a magnitude of the measured acceleration exceeds a predetermined threshold.

Alternatively, the processor is adapted to determine that the sensor module has suffered an impact if the magnitude of the acceleration measured in a specified direction exceeds a predetermined threshold.

Alternatively, the processor is adapted to determine that the sensor module has suffered an impact if a variance of the measurements from the accelerometer exceeds a predetermined threshold.

Preferably, the processor is further adapted to identify an impact time, the time at which the sensor module suffered the impact.

Preferably, the processor is adapted to identify the impact time by examining a time stamp of the measured accelerations.

Preferably, the processor is further adapted to identify an onset time, the time at which the sensor module started to move prior to the impact.

Preferably, the processor is adapted to identify the onset time by examining the measured accelerations before the impact to identify a stable period in which the measured accelerations vary by less than a predetermined threshold, and to identify the onset time as the time at which the stable period ends.

Alternatively, or in addition, the processor is adapted to identify the onset time by examining the measured accelerations before the impact to identify a variation in the direction of the measured acceleration that is above a predetermined threshold, and to identify the onset time as the time at which the variation in the direction first exceeded the threshold.

Preferably, the processor is adapted to estimate the vertical displacement of the sensor module by twice integrating the measurements from the accelerometer between the onset time and impact time.

Preferably, the processor is adapted to estimate the gravitational acceleration at the onset time by identifying the component of the measured acceleration at the onset time that acts in a vertical direction.

Preferably, the processor is adapted to subtract the estimated gravitational acceleration from the measurements that are used by the processor to estimate the vertical displacement of the sensor module.

Preferably, the personal fall detection system comprises means for determining if a fall has taken place using the estimated vertical displacement from the sensor module.

Preferably, the means is further adapted to trigger an alarm if it is determined that a fall has taken place.

In some embodiments, the processor is part of the sensor module. However, in other embodiments, the processor is part of a base unit that is separate to the sensor module.

According to a second aspect of the invention, there is provided a method comprising measuring accelerations acting on an object; analyzing the measured accelerations to determine if the object has suffered an impact; estimating a vertical displacement of the object during a time period immediately before the impact by twice integrating the measurements from the accelerometer.

According to a third aspect of the invention, there is provided a computer program for performing the method described above when executed on a computer.

BRIEF DESCRIPTION OF THE DRAWINGS

The invention will now be described, by way of example only, with reference to the following drawings, in which.

DETAILED DESCRIPTION OF THE PREFERRED EMBODIMENTS

Figure 1:
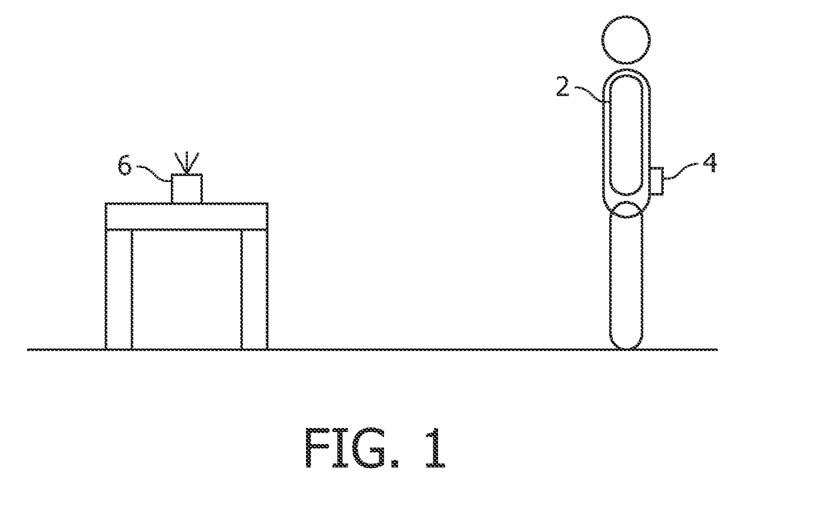
FIG. 1 shows a fall detection system in accordance with the invention.

FIG. 1 shows a fall detection system in use by a user 2. The fall detection system comprises a sensor module 4 that is worn by the user 2 and a base unit 6. The sensor module 4 can be worn on any part of the user's body, but it is preferred that it is worn around the user's waist or chest in order to improve the detection of any falls.

The sensor module 4 comprises at least an accelerometer for measuring the acceleration experienced by the sensor module 4 and some means for communicating with the base unit 6. If the sensor module 4 detects a fall or other alarm condition, the sensor module 4 communicates with the base unit 6, and the base unit 6 can issue or trigger an alarm.

In alternative embodiments, the functionality of the sensor module 4 and base unit 6 can be combined into a single device.

Figure 2:
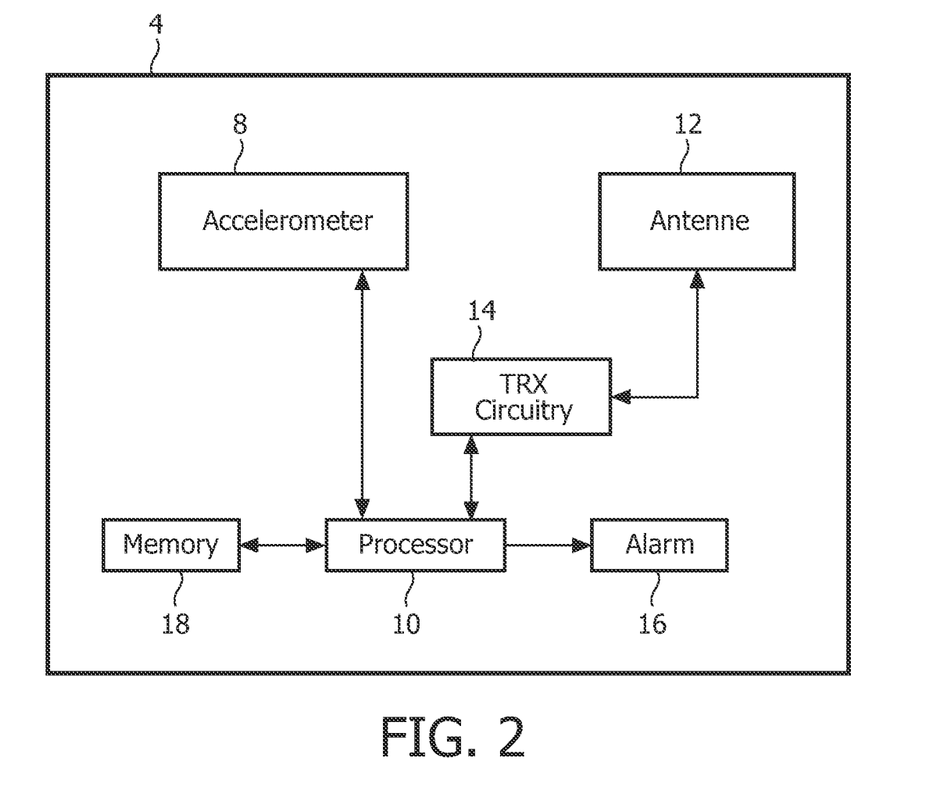
FIG. 2 is a block diagram showing the sensor module of the fall detection system in more detail.

FIG. 2 shows the sensor module 4 in more detail. In this embodiment, the sensor module 4 comprises an accelerometer 8 that measures the acceleration experienced by the sensor module 4 in three dimensions, and a processor 10 for determining whether a fall has taken place from the accelerometer 8 measurements. The accelerometer 8 can measure the acceleration continuously or at discrete intervals and can time-stamp each measurement (although it is possible for the processor 10 to time-stamp the measurements as they are written into the memory 18). The sensor module 4 also comprises an antenna 12 and associated transceiver circuitry 14 for communicating with the base unit 6, an alarm unit 16 for issuing an alarm signal or tone in the event that an alarm condition is detected and a memory 18 for storing a set of measurements from the accelerometer 8.

In a preferred embodiment, the memory 18 is a circular buffer or similar type of device that continuously or periodically stores the measurements covering a particular time period from the accelerometer 8 for subsequent retrieval by the processor 10. Thus, when the memory 18 is full, further measurements will overwrite the oldest measurements stored in the memory 18 so that the memory 18 contains the n most recent accelerometer measurements covering a specific time interval T preceding the present. Clearly, the memory 18 must have sufficient capacity to store accelerometer measurements covering at least the time taken for a fall. For example, a memory 18 that can store accelerometer measurements covering a period of five seconds should be sufficient for implementing the invention.

In accordance with the invention, the displacement of the sensor module 4 is estimated by twice integrating the measurements from the accelerometer 8. By making this displacement estimation available to a fall detection algorithm executing in the processor 10, the performance of the false alarm rate of the fall detection system can be improved.

Figure 3:
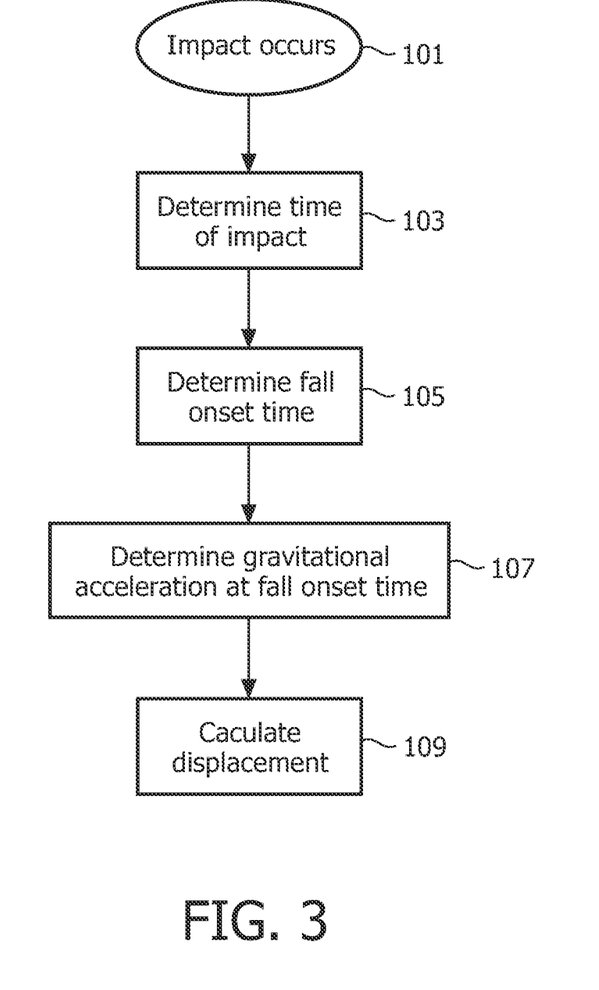
FIG. 3 is a flow chart illustrating a method in accordance with the invention.

FIG. 3 illustrates a method of estimating the displacement of the sensor module 4 in accordance with an embodiment of the invention. The method starts at step 101 when an impact occurs. An "impact" is defined as a measurement or set of measurements from the accelerometer 8 that are characteristic of a collision with a solid object, such as the ground. In particular, an impact can be a measurement whose magnitude exceeds a predetermined threshold or a measurement along a particular axis or in a particular direction whose magnitude exceeds a predetermined threshold. Alternatively, as an impact will result in a large variance in the output from the accelerometer 8, an impact can be identified by comparing the variance in the measurements to a predetermined threshold. The processor 10 can identify the impact by examining the measurements from the accelerometer 8 as they are stored in the memory 18.

As described above, the accelerometer 8 continuously or periodically provides measurements of the acceleration to the memory 18 for storage. Therefore, at the point that the processor 10 determines that an impact has occurred (which may be shortly after the impact has occurred due to processing delays or through confirming the fall by examining subsequent accelerometer measurements), the memory 18 will contain measurements of the acceleration covering a time interval T.

In step 103, the processor 10 determines the time that the impact occurred. To do this, the processor 10 examines the accelerometer measurements stored in the memory 18 to identify the highest or peak acceleration measurement that is associated with the impact. If the accelerometer 8 provides separate measurements of the acceleration along each of the three-dimensional axes, the processor 10 can examine the magnitude of the acceleration vector to determine the highest or peak acceleration.

Once the peak measurement is found, the time of the measurement is determined from the associated time-stamp, and this time is recorded as $t_{impact}$.

Once the impact time has been determined, the method identifies the time at which the fall started $t_{onset}$ (step 105).

Preferably, the method determines $t_{onset}$ from the accelerometer measurements stored in the memory 18. To do this, the processor examines the accelerometer measurements in the memory 18 preceding the measurement at time $t_{impact}$ to identify if the measurements exhibit a stable period where the magnitude and/or direction of the acceleration measured by the accelerometer 8 do not significantly vary.

In particular, it has been noted that measurements by an accelerometer 8 before a fall starts are generally stable, in that the variance of the measurements is below a predetermined threshold. Therefore, the processor 10 can examine the measurements stored in the memory 18 for a stable period preceding the impact at $t_{impact}$, and the time that the fall started can be determined as the time associated with the accelerometer measurement at the end of this stable period.

In addition or alternatively to the above, the direction of the acceleration measured by the accelerometer 8 can start to change at the onset of a fall, so the processor 10 can examine the stored measurements to identify a period before the impact time $t_{impact}$ in which the direction starts to change at a rate that is higher than a predetermined threshold. The fall onset time $t_{onset}$ can be determined as the time associated with the accelerometer measurement at the start of this period of direction change.

If the processor 10 identifies an onset time using both of these methods, the processor 10 can take an average of the times to use as $t_{onset}$.

If the processor 10 is unable to identify a stable period in the stored measurements or a period in which the direction of the acceleration starts to change (or if the processor 10 wants to verify the reliability of either or both of these measurements), the processor 10 can estimate the onset time using the following:

From $$H = \frac{1}{2} g t_{fall\_duration}^2 \quad (1)$$

where H is the height displacement, g is acceleration due to gravity, and $t_{fall\_duration}$ is the duration of the fall, we obtain:

$$t_{fall\_duration} = \sqrt{\frac{2H}{g}} \quad (2)$$

Therefore, if the height displacement is assumed to be around 0.8 to 1 meter (based on the sensor module being worn around a user's waist, the time at which the fall started can be determined from:

$$t_{onset} = t_{impact} - t_{fall\_duration} \quad (3)$$

It will be appreciated that this value for $t_{onset}$ is only strictly suitable for an object or person in free fall, but it is used here as an approximate value for normal (non-free) falls.

In step 107, the processor 10 estimates the gravitational acceleration on the accelerometer 8 when the fall started (i.e. at time $t_{onset}$). This is done by identifying the component of the accelerometer 8 measurement at $t_{onset}$ (or just before $t_{onset}$) that corresponds to gravity. If it is assumed that the y-axis of the accelerometer 8 is perpendicular to the ground (see FIG. 4), the processor 10 can estimate the gravitational acceleration on the accelerometer 8 at $t_{onset}$ by taking the y-component of the $t_{onset}$ measurement.

In step 109, the processor 10 calculates the displacement that has taken place during the fall.

Figure 4:
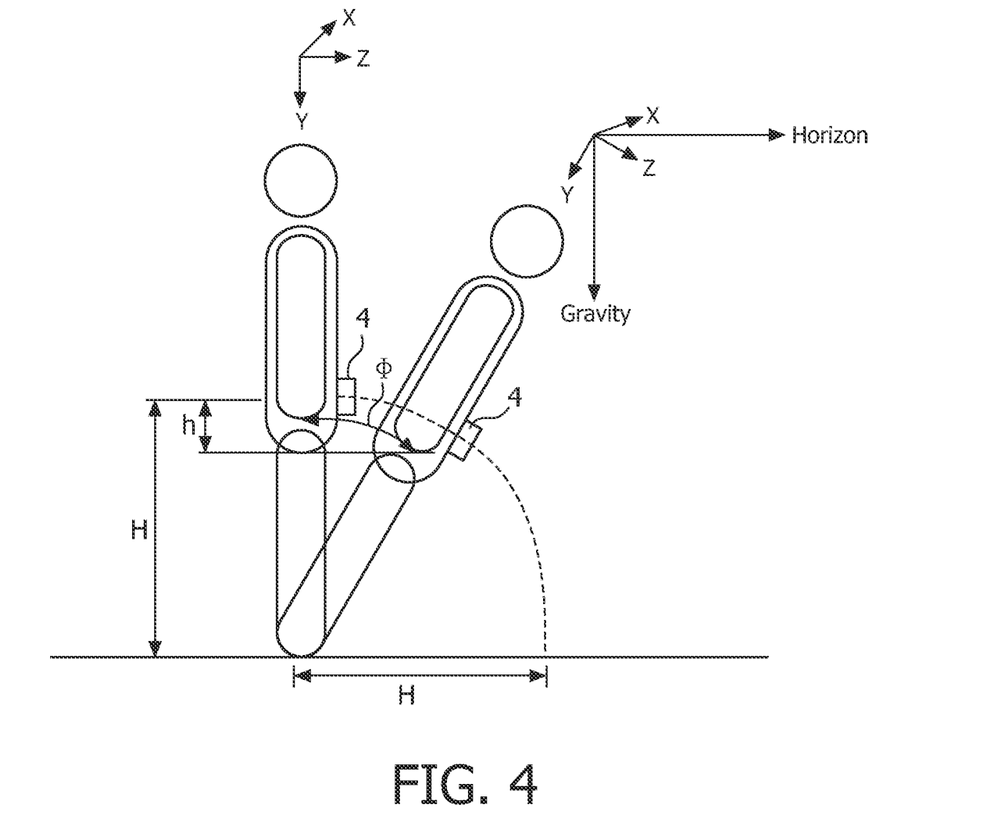
FIG. 4 is an illustration of a sensor module and user falling.

As shown in FIG. 4, it is assumed that the sensor module 4 is attached to the user's waist and that the y-axis of the accelerometer 8 in the sensor module 4 is pointing downwards, in the direction that gravity will act when the sensor module 4 is in its normal orientation.

The acceleration represented by the measurements from the accelerometer 8 is a superposition of gravity and accelerations caused by external forces. As the external forces on the sensor module 4 at the fall onset time $t_{onset}$ are unknown, the displacement calculated in this step is an approximate value.

It will be appreciated that it is only necessary to calculate the displacement in the gravity direction. Therefore, the acceleration in the x, y and z axes must be mapped to the gravity direction according to the orientation of the sensor module 4. However, it can be seen in FIG. 4 that the orientation of the sensor module 4 changes during a fall, because the sensor module 4 follows an arc to the floor instead of a straight line downwards.

In the approximation, it is assumed that the initial force acting in the gravity (y-axis) direction is zero. Therefore, equation (3) can be used to estimate the fall onset time $t_{onset}$.

In most cases of a forward/backward (i.e. along the z-axis) or left/right side (i.e. along the x-axis) fall, one axis will always be perpendicular to the direction in which gravity acts and can be omitted from the calculation, since gravity will not have a component along that axis during the fall. For example, in the forward fall illustrated in FIG. 1, the x-axis does not need to be considered.

In forward/backward falls, the accelerations along the y-axis and z-axis contribute to the vertical displacement via the angle Φ (it is assumed that the x-axis is perpendicular to the direction in which gravity acts at all times during the fall). The angle Φ can be estimated by $$\Phi = \arccos(y/r) \quad (4)$$

where $$r = \sqrt{x^2 + y^2 + z^2} \quad (5)$$

Since the measurements from the accelerometer 8 will consist of two parts, gravity and the other accelerations on the sensor module 4, gravity is compensated for by subtracting the initial y-axis measurement $y_{initial}$ obtained in step 107.

The displacement of the sensor module 4 during the fall can then be obtained from the y- and z-axis components of the measurements over the period $t_{fall\_duration}$ by evaluating equation (6) below.

$$H = \int\int_{t_{fall\_duration}} (y\cos\Phi + z\sin\Phi - y_{init}) \, dt\, dt \quad (6)$$

$$H = \int\int_{t_{fall\_duration}} \left( \frac{-y^2}{\sqrt{x^2+y^2+z^2}} + z\sqrt{\frac{x^2+z^2}{x^2+y^2+z^2}} - y_{init} \right) dt\, dt$$

$$H = \int\int_{t_{fall\_duration}} \left( \frac{y^2 + z\sqrt{x^2+z^2}}{\sqrt{x^2+y^2+z^2}} - y_{init} \right) dt\, dt$$

Figure 5:
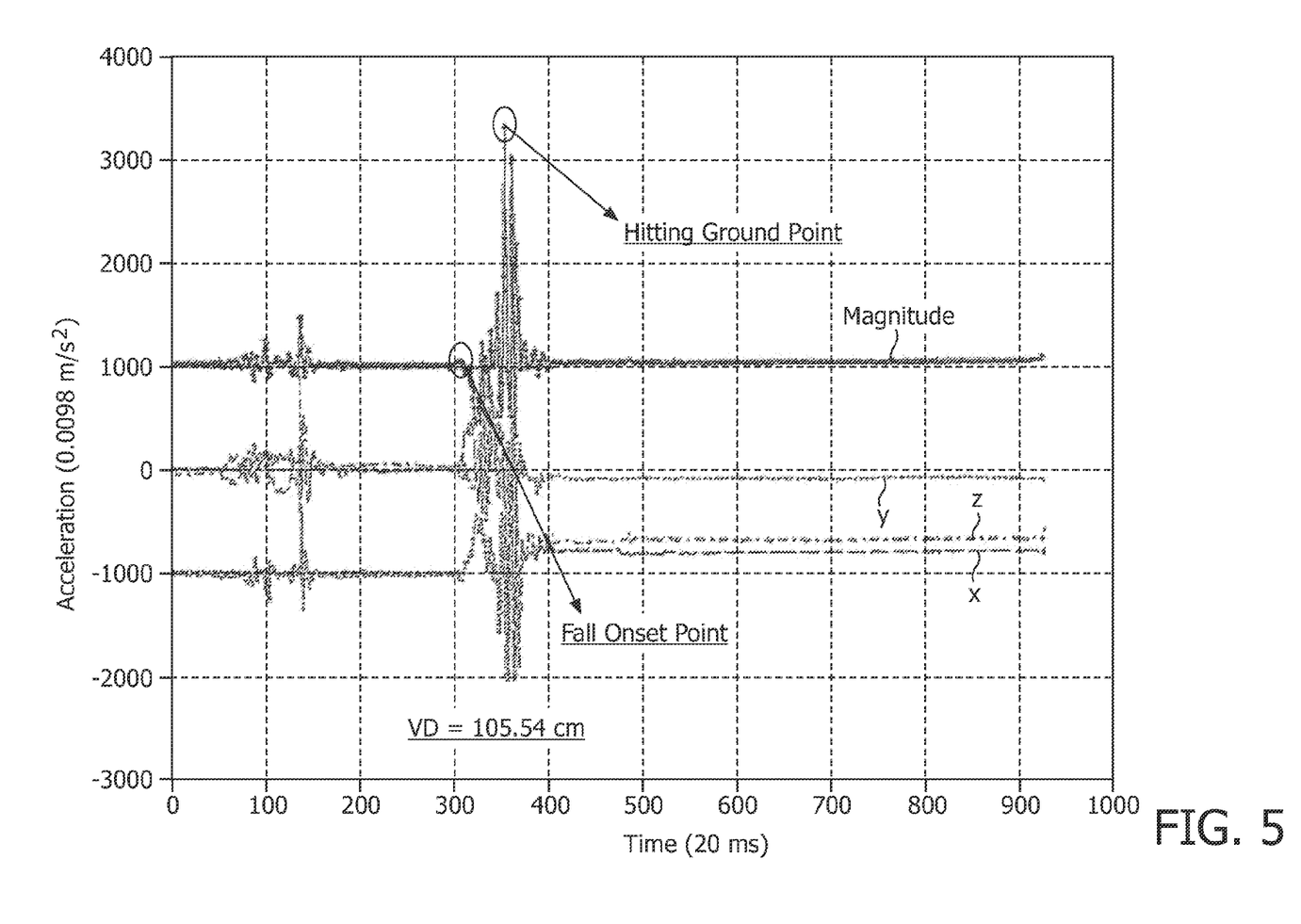
FIG. 5 is a graph showing some exemplary measurements from an accelerometer.

FIG. 5 shows an exemplary graph illustrating a displacement calculation in accordance with the invention. The three lines represent the x-, y- and z-axis measurements from the accelerometer 8 for the time interval T for a forward fall. The displacement calculation twice integrates the acceleration measurements between the fall onset point and the "hitting ground" point, and results in a vertical displacement of 105.54 centimeters.

It will be appreciated that the above algorithm calculates the displacement when the fall is a forward fall or a backward fall. Based on same principle, if the fall is a left or right side fall, the x-axis and y-axis readings will be used in the calculation.

In a more general case, all components of acceleration will be used in the displacement calculation. In this case, the displacement is calculated by evaluating $$H = \int\int_{t_{fall\_duration}} (y\cos\Phi + x\sin\Phi_x + z\sin\Phi_z - \Omega\cos\Phi) \, dt\, dt \quad (7)$$

$$H = \int\int_{t_{fall\_duration}} \left( \frac{-y(y-\Omega)}{\sqrt{x^2+y^2+z^2}} - \frac{x^2}{\sqrt{x^2+y^2}} + \frac{z^2}{\sqrt{y^2+z^2}} \right) dt\, dt$$

where $\Phi_x$ and $\Phi_z$ are the components of $\Phi$ in the X-Y and Y-Z planes respectively, and $\Omega$ is the acceleration due to gravity (9.8 ms$^{-2}$).

The displacement estimation algorithm presented above can be integrated into a fall detection system that also includes orientation and impact detection. When the sensor module detects an orientation change and a big impact, it will ascertain the time of impact $t_{impact}$ and calculate the displacement. If the displacement value is reasonable (say 0.5 to 1.5 meters), then the processor 10 can classify the impact as a fall, otherwise, the processor 10 can ignore the impact.

For example, the user may suddenly rotate the sensor module 90 degrees in their hands and generate a big impact, but the calculated displacement will be near to zero, so the processor 10 will decide that a fall has not taken place.

The displacement calculation according to the invention provides the advantages that the false alarm rate of detecting falls can be improved, no height sensor is needed, which may increase the energy consumption and volume of the sensor module 4 and that as the complexity of the quadratic integration calculation is low, it can be easily exploited in a sensor module for a fall detection system.

Although the invention has been described as implemented completely in the sensor module, it will be appreciated that part of the method can be implemented by a processor in the base unit 6 of the personal fall detection system. For example, the sensor module 4 can transmit all accelerometer measurements to the base unit 6 for analysis by a processor in that unit 6.

In addition, although the invention provides a method and apparatus for approximately determining a change in height of a sensor module resulting from a fall, based only on measurements made by an accelerometer, it will be appreciated that the invention can be used to determine displacement during other events that have characteristic start and end points represented in the accelerometer measurements, and in which the orientation of the accelerometer may change.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope. A computer program may be stored/distributed on a suitable medium, such as an optical storage medium or a solid-state medium supplied together with or as part of other hardware, but may also be distributed in other forms, such as via the Internet or other wired or wireless telecommunication systems.

The invention claimed is:

1. A personal fall detection system configured to be attached to a user, the system comprising:
   an accelerometer configured to measure acceleration along at least two directions and output time stamped signals indicative of the measured acceleration; and
   a computer processor configured to:
      receive the time-stamped signals,
      from the time stamped signals, determine occurrence of an impact and an impact time at which the impact occurred,
      from the time stamped signals time stamped with times preceding the impact time, determine an onset time at which acceleration that ended with the detected impact started,
      calculate a gravitational acceleration at the onset time from the measured acceleration in the vertical direction at the onset time,
      from the time stamped signals between the onset time and the impact time, determine a vertical displacement of the accelerometer that occurred between the onset time and the impact time,
      classifying the impact as a fall and determining an alarm condition when the vertical displacement is between 0.5 and 1.5 m.

2. The personal fall detection system according to claim 1, wherein the processor is further is configured to:
   subtract the gravitational acceleration from the measured acceleration between the onset time and the impact time.

3. The personal fall detection system according to claim 1, further including:
   a transceiver and an antenna configured to transmit an alarm signal when the impact is classified as a fall.

4. The personal fall detection system according to claim 1, wherein the computer processor is configured to determine the occurrence of the impact in response to the measured accelerations being characteristic of a collision with a solid object.

5. The personal fall detection system according to claim 4, wherein the acceleration characteristic includes a change in the acceleration exceeding a predetermined threshold and wherein the processor is configured to determine the occurrence of the impact in response to changes in the measured acceleration exceeding the predetermined threshold.

6. The personal fall detection system according to claim 1, wherein the computer processor is configured to determine the onset time from the time stamped signals which are time stamped with times preceding the impact time by identifying at least one of:
   (a) a stable period in which the measured accelerations vary by less than a predetermined time threshold, the onset time being the time at which the stable period ends, and
   (b) a variation in a direction of the measured acceleration that is beyond a predetermined acceleration variation threshold, the onset time being the time at which the variation in direction exceeded the acceleration variation threshold.

7. The personal fall detection system according to claim 1, wherein the computer processor is configured to:
   determine a first onset time from a time at the end of a stable period; and
   determine a second onset time from a time at which a variation in direction exceeds an acceleration variation threshold.

8. The personal fall detection system according to claim 1, further including:
   an alarm configured to issue an alarm signal in the event the alarm condition is determined.

9. The personal fall detection system as claimed in claim 7, wherein the processor is configured to:
   determine both a first vertical displacement from the measured acceleration between the first onset time and the impact time and a second vertical displacement from the measured acceleration between the second onset time and the impact time.

10. A method of detecting a fall, the method comprising:

from time-stamped acceleration signals indicative of acceleration along at least two directions from an accelerometer configured to measure acceleration along two directions and output the time-stamped acceleration signals, determining occurrence of an impact and a time of the impact with a computer processor;

from the measured acceleration preceding the impact time, determining an onset time with the computer processor;

from the measured acceleration between the onset time and the impact time, determining a first vertical displacement which the accelerometer fell between the onset time and the impact time with the computer processor;

recalculating the onset time with the computer processor;

determining a second vertical displacement from the measured acceleration between the recalculated onset time and the impact time with the processor;

determining whether the first and second vertical displacements are between 0.5 and 1.5 m, with the computer processor;

classifying the occurrence of the impact as a fall when the vertical displacements are determined to be between 0.5 and 1.5 m with the processor;

in response to classifying the occurrence of the impact as a fall, at least one of communicating an alarm signal with an antenna and a transceiver and causing an alarm to issue an alarm signal.

11. The method according to claim 10, wherein detecting the onset time includes:

examining the measured acceleration preceding the impact time to locate a stable time in which the measured acceleration varies less than a predetermined threshold;

selecting a time at the end of the stable time as the onset time.

12. The method according to claim 10, wherein determining the onset time includes:

examining the measured accelerations prior to the impact time to identify variations in a direction of the acceleration;

selecting a time at which the variation in the direction of the measured acceleration first exceeded a direction variation threshold as the onset time.

13. A non-transitory computer-readable medium carrying software configured to control the computer processor to perform the method of claim 10.

14. A personal fall detection system comprising:

an accelerometer configured to measure acceleration along at least two directions;

a processor configured to:

from the measured acceleration, determine an impact and a time of the impact;

from the measured acceleration preceding the impact time, determine a first onset time;

from the measured acceleration between the first onset and impact times, determine a first vertical displacement which the accelerometer fell between the first onset time and impact time;

determine the onset time a second time using a different onset time determining technique;

determine a second vertical displacement from the measured acceleration between the second onset time and the impact time;

compare the first and second vertical displacements with a height between 0.5 and 1.5 m to determine whether a fall occurred.

15. The personal fall detection system according to claim 14, wherein the processor is configured to determine one of the first and second onset times by:

examining the measured acceleration preceding the impact time to locate a stable time in which the measured accelerations vary less than a predetermined threshold;

selecting a time at the end of the stable time as the onset time.

16. The personal fall detection system according claim 14, wherein the processor is configured to determine one of the first and second onset times by:

examining the measured accelerations prior to the impact time to identify variations in a direction of the acceleration;

selecting a time at which the variation in the direction of the measured acceleration first exceeded a direction variation threshold.

17. The personal fall detection system according to claim 14, further including:

an antenna and a transceiver configured to communicate an alarm signal in response to determining that the fall occurred.

18. The personal fall detection system according to claim 14, further including:

an alarm configured to issue an alarm tone in response to determining that the fall occurred.

19. A personal fall detection system comprising:

an accelerometer configured to measure acceleration along at least two directions;

a processor configured to:

from the measured acceleration, determine an impact and a time of the impact;

from the measured acceleration preceding the impact time, determine a first onset time using a first onset time determining technique;

determine an onset time a second time using a second onset time determining technique, the second onset time determination technique being different from the first onset time determining technique;

averaging the first and second onset times to generate an average onset time;

determine a vertical displacement between the average onset time and the impact time;

compare the vertical displacement with a height between 0.5 and 1.5 m to determine whether a fall occurred.

20. The personal fall detection system according to claim 19, further including:

a transceiver and an antenna configured to transmit an alarm signal when the impact is determined to be a fall.

21. The personal fall detection system according to claim 19, further including:

an alarm configured to issue an alarm signal when the impact is determined to be a fall.

* * * * *